United States Patent [19]

Rand et al.

[11] 4,392,040

[45] Jul. 5, 1983

[54] INDUCTION HEATING APPARATUS FOR USE IN CAUSING NECROSIS OF NEOPLASM

[76] Inventors: Robert W. Rand, 521 N. Bristol Ave., Los Angeles, Calif. 90049; Harold D. Snow, 4201 Noble Ave., Sherman Oaks, Calif. 91403; David G. Elliott, 737 W. Startlight Hights, La Canada, Calif. 91011; Glenn M. Haskins, 3811 Rio Hondo Ave., Rosemead, Calif. 91770

[21] Appl. No.: 223,727

[22] Filed: Jan. 9, 1981

[51] Int. Cl.³ .............................................. H05B 6/44
[52] U.S. Cl. ........................... 219/10.71; 219/10.49 R; 219/10.57; 219/10.75; 219/10.79; 128/1.5
[58] Field of Search ............... 219/10.71, 10.75, 10.77, 219/10.79, 10.57, 10.61, 10.49 R, 10.43; 128/1.5

[56] References Cited

U.S. PATENT DOCUMENTS

| | | | |
|---|---|---|---|
| 1,980,875 | 11/1934 | Northrup | 219/10.61 X |
| 3,478,156 | 11/1969 | Segsworth | 219/10.75 X |
| 4,066,065 | 1/1978 | Kraus | 128/1.5 |
| 4,106,488 | 8/1978 | Gordon . | |
| 4,266,533 | 5/1981 | Ryaby et al. | 128/1.5 |
| 4,303,636 | 12/1981 | Gordon . | |
| 4,317,979 | 3/1982 | Frank et al. | 219/10.49 R X |

Primary Examiner—B. A. Reynolds
Assistant Examiner—Philip H. Leung
Attorney, Agent, or Firm—Edward D. O'Brian; K. H. Boswell

[57] ABSTRACT

Induction heating can be utilized to cause necrosis of neoplasm as a result of hyperthermia by a process involving the injection of particles having hysteresis heating characteristics into tissue either within or in close proximity to the neoplasm and then subjecting these particles to an alternating magnetic field sufficient to cause hysteresis heating. The frequency of the field is preferably sufficiently low so as to minimize eddy current and dielectric heating. The particles used are preferably initially located within a biologically inert liquid carrier which will facilitate the insertion of the particles within the body and which will automatically become non-liquid within the body so as to hold the particles in place. The actual heating is preferably carried out by positioning either the entire patient or the affected portion of the patient's body through a series of axially aligned, parallel, liquid cooled coils. Only one of these coils is connected to a power supply.

7 Claims, 2 Drawing Figures

INDUCTION HEATING APPARATUS FOR USE IN CAUSING NECROSIS OF NEOPLASM

BACKGROUND OF THE INVENTION

The invention set forth in this specification pertains to a new and improved method and apparatus for causing necrosis of neoplasm by hyperthermia.

Aberrant cells within the body, such as are frequently referred to as neoplasm, are the subject of a great deal of concern to society and civilization because of the very undesirable consequences of various growths such as are commonly referred to as tumors, cancers and the like. Tremenduous sums of money have been and will continue to be spent in connection with the problem of causing necrosis of neoplasm with a minimal detrimental effect to a person at a minimal cost. It is considered that no one approach to this problem of causing necrosis of neoplasm will ever be completely satisfactory for use with all different types of neoplasms.

It has been recognized that certain types of neoplasms can be effectively necrosed as the result of the use of hyperthermia. In the past, the heating used in this type of treatment has been achieved either through the use of the electromagnetic radiation associated with a radio frequency or microwave field or through the use of an alternating magnetic field such as is associated with induction heating. It is considered that an understanding of the present invention requires an understanding as to essential differences between these two distinctly different types of heating.

A radio frequency or microwave field can only be utilized in causing heating at or adjacent to the surface of a body because of the tendency of the body to absorb radio frequency electromagnetic radiation. The depth of which such radiation will penetrate the body will very depending upon the frequency of the radiation. Such body tissue heating as is caused by radio frequency radiation has two principal components: eddy current heating and dielectric heating. Both result from the electromagnetic field employed contacting the tissue. Effective heating of this type can be achieved in the absence of any foreign material in tissue being heated.

As opposed to this, induction heating of body tissue as a result of the presence of a material having hysteresis characteristics may be referred to or at least considered as hysteresis heating. It is based upon the use of a magnetic field which is normally presumed to be unattenuated by tissue. Hence, induction heating can reach any desired depth or level beneath the surface of tissue. In order to achieve this manner of heating in tissue, it is necessary to locate a material exhibiting magnetic hysteresis at or about the location where heat is desired. Any such induction-hysteresis heating will be accompanied by some eddy current and dielectric heating.

The amount of eddy current and dielectric heating can be minimized by utilizing a comparatively low frequency alternating magnetic field. The amount of such heating varies directly with the square of the frequency of the field. As opposed to this, the amount of hysteresis heating forming the operative "part" of induction heating for use with the present invention varies directly with the frequency. Thus, in general, the lower the frequency of the field the less the amount of undesired eddy current heating achieved relative to the amount of the desired hysteresis heating achieved. The frequency used, however, should not be so low as to preclude the achievement of a desired degree of hysteresis heating.

The limited amount that a radio frequency field can normally penetrate body tissue has been and remains an important factor limiting the use of this type of heating in the treatment of various different neoplasms. Obviously, this radio frequency heating can not be utilized effectively in causing hyperthermia in aberrant growths which are sufficiently beneath the surface of tissue so as not to be reached by a radio frequency field. The use of such a field to cause hyperthermia at or adjacent to the surface of the skin or at or adjacent to the interior of an incision within the body is limited by another important factor—the problem of selectively concentrating the heat developed so that neoplasm is heated to a point sufficient to cause necrosis without there being a related or corresponding heating of adjacent normal tissue.

This can be easily illustrated by referring to specific temperatures such as have previously been recognized to be important in causing necrosis as a result of hyperthermia. It is usually considered that necrosis will not be caused by the exposure of most body tissue to a temperature of about 40° C. for a reasonably prolonged period. It is also generally considered that if commonly found body tissue—including neoplasms—are held at a temperature of at least 42° C. for a reasonably prolonged period that such cells or tissue will be destroyed if the period is adequately long for the purpose.

It is also generally conceded that commonly encountered cells and tissue—including neoplasms—will be necrosed by exposure to a temperature of from about 60° C. or, of course, a higher temperature for a very minimal or limited, practically instantaneous time period. It should be noted that body tissue should not normally be subjected to a temperature reasonably approaching 100° C. for even a very short, instantaneous time period because of the possibility of the vaporization of water in the body and the attendant possibility of damage being caused by the sudden expansion of vaporization of water. As a practical matter, it is considered that internally the body should never be heated past 90° C. to avoid any possibility of such vaporization.

Apparently, the relationship between the time that neoplasm or other body growth need be exposed to a specific temperature to cause necrosis and the time necessary for such exposure to cause necrosis are not related in exactly usual time-temperature manner applicable to the usual temperature reactions. Further, certain parts of the body or neoplasms are more susceptible to necrosis at an elevated temperature than other parts of the body and/or other certain neoplasms. Because of these factors, it is impossible to give exact relationships between the time and the temperature necessary to accomplish necrosis and, in particular, necrosis of neoplasms. Another factor which will be important in considering the amount of hyperthermia to cause necrosis in neoplasm will involve the tendency of the body and/or a particular portion of the body to serve to at least a degree as a heat insulator so as to tend to concentrate heat developed as, for example, at a specific source.

With radio frequency or microwave hyperthermia the difficulty in confining the field necessary to cause necrosis of a specific area or region will normally cause necrosis of healthy tissue in an adjacent area or region. While to a degree this can be combated through the use of specialized electrodes, it is not considered that it is possible to adequately control radio frequency or microwave heating in many applications so as to avoid detrimental damage to normal cells or tissue. While it may be possible to improve the concentration of the heating effects achieved with radio frequency or microwave heating through the implantation of a metallic conductor or another similar material in a specific area where concentrated heating is desired, it is considered that such a use of a conductor is not always advantageous because such a conductor will not improve the depth of penetration of tissue by a radio frequency field.

The use of induction heating in causing necrosis of neoplasm is considered desirable in overcoming several problems involved in utilizing a radio frequency field to cause hyperthermia leading to necrosis of neoplasm as noted in the preceding. When induction heating is used for this purpose, it is necessary to utilize an invasive technique to locate a material having a magnetic permeability greater than unity and capable of exibiting hysteresis losses—for example, ferromagnetic particles such as a conventional ferrite or conventional iron or steel powders—in or immediately adjacent to the neoplastic growth. The use of such a magnetic material in an alternating magnetic field results in hysteresis heating within the magnetic material itself. This localized or focused hysteresis heating overcomes the problem of containing or limiting the heated area obtained with a radio frequency field. Because of the penetration of a low frequency magnetic field with respect to body tissue, it is possible to use a magnetic material well beneath the surface of the body.

From this it is believed that it will be apparent that the utilization of induction hysteresis heating in connection with the hyperthermia of neoplasm has a great deal of advantageous potential. Unfortunately, it is not considered that the prior efforts for accomplishing necrosis of neoplastic growth by induction heating have been sufficiently effective and desirable for this purpose. It is considered that several factors may be important in connection with this.

One of these concerns the lack of availability of induction heating equipment which is specifically adopted for use in treating a body such as a human or animal body in which magnetic material has been implanted so as to produce localized heating. In connection with this, it is noted that prior induction heating coils have not normally been designed with the intent that they be utilized to provide a very intense AC magnetic field over a comparatively large volume so as to cause heating in a specific, very limited area or region coming within the "scope" of the complete magnetic field produced by the coil in which material capable of hysteresis heating is located. It is considered that this factor has led to a degree of inefficiency of prior induction heating coils when such coils have been utilized in conjunction with body tissue so as to cause induction heating of materials or particles embedded within such tissue.

It is considered, however, that the prior procedures for accomplishing necrosis of neoplastic growths by hysteresis heating have also been comparatively unsatisfactory for other reasons relating to the technique or procedure followed in implanting the magnetic material or particles used. In general, such materials have not been utilized in such a manner as to be effectively immobilized either within or immediately adjacent to a neoplasm so as to be capable of providing a localized heating without danger of the magnetic material used moving from its initial location within the body. Any such movement would be highly disadvantageous because of the possibility of undesired interference with the normal operation of the body.

BRIEF SUMMARY OF THE INVENTION

Because of these various related considerations, it is considered that there is a need for a new and improved process of causing necrosis of neoplasm as a result of hyperthermia of the neoplasm which may be easily and conveniently carried out at a comparatively nominal cost and which is effective for its intended purpose. The invention is intended to provide such a process. A further "process" objective of this invention is to provide a procedure as indicated which can be utilized in connection with a wide variety of different neoplasms located in various different regions of the body without significantly endangering the life or health of the body in which such neoplasms are located.

In accordance with this invention, those aspects of the invention which are directed towards the process as noted are achieved by providing a process of causing necrosis of neoplasm as a result of hyperthermia of the neoplasm in which magnetic particles are injected into tissue in proximity with the neoplasm and are subjected to an alternating magnetic field so as to cause hysteresis heating of said particles in which the improvement comprises: said particles are mixed with a carrier fluid as they are injected into said tissue, said carrier fluid being biologically inert and being capable of becoming non-fluid within said tissue, and causing said carrier fluid to become non-fluid within said tissue.

As a result of the considerations indicated in the preceding, it is also considered that there is a need for a new and improved apparatus for use in causing induction hysteresis heating of specific regions or areas within a much larger region or area such as within a living body. An objective of the present invention is to fulfill this need. The invention is also intended to provide an apparatus for the purpose of which may be easily and conveniently constructed at a comparatively nominal cost, which is effective for its intended utilization, and which is desirable from an energy utilization standpoint, particularly when this is related to the results accomplished or achieved with the apparatus.

In accordance with this invention, those aspects of the invention which are directed towards an apparatus are achieved by providing an induction heating apparatus having a series of separate induction heating coils and means for passing an alternating current through said coils at a frequency sufficient to cause induction heating in which the improvement comprises: a capacitor means associated with each of said coils, each capacitor means being connected across the terminals of the coil with which it is associated so as to form a physically separate circuit, said coils being located in axial alignment with one another and being located immediately adjacent to one another, only one of said coils being connected to said means for passing AC current.

BRIEF DESCRIPTION OF THE DRAWINGS

Because of the nature of this invention, it is considered that it is best more fully explained with reference to the accompanying drawing in which.

Figure 1:
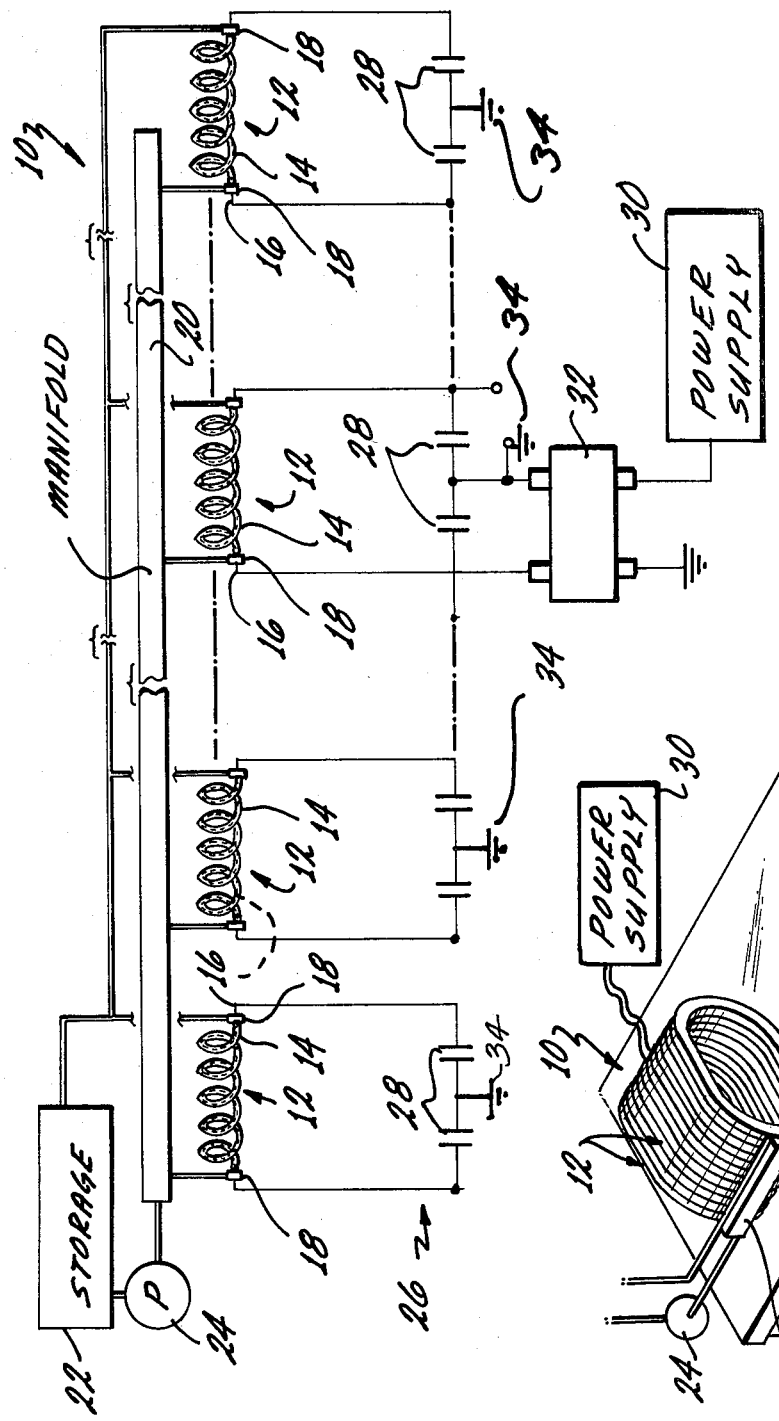
FIG. 1 is a diagramatic view illustrating the essential features or concepts of a presently preferred embodiment or form of an apparatus in accordance with this invention.
Figure 2:
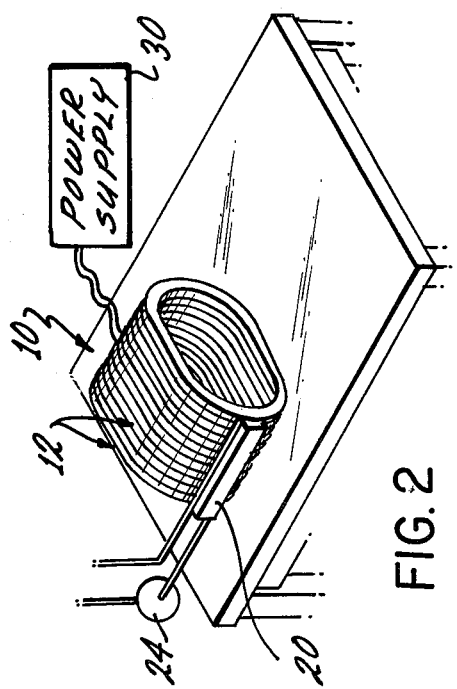
FIG. 2 is an isometric view showing the configuration and utilization of the coils explained.

It is to be understood that the illustration of a particular apparatus shown is not to be taken as limiting this invention in any respect. This invention involves the concepts or principals set forth and defined in the appended claims. Those skilled in the field of utilizing induction heating in treatment of neoplasm will realize that these concepts or principals may be utilized in various different ways without departing from the scope of the subject matter set forth in the claims.

DETAILED DESCRIPTION

As indicated in the preceding summary, an important aspect of the invention involves the formation of a mixture of magnetic particles and a carrier fluid. This mixture should have fluid or fluid like properties enabling the complete mixture to be easily and conveniently injected into a body through the use of a conventional hypodermic needle or any other reasonably related procedure such as, transarterial catherization. This intended manner of location of a mixture within the body places several important restrictions upon the ingredients of the mixture.

Within the broad purview of the present invention, it is possible to utilize any magnetic material having a magnetic permeability greater than unity which exhibits hysteresis heating. As a practical matter, it is desired to utilize only magnetic materials which present a minimum of a toxicity problem when used within the human body and in addition which possess or exhibit as large a hysteresis loop when subjected to an alternating magnetic field as reasonably obtainable. It is the area within such a loop that is of prime importance in the present invention since such area corresponds with the efficiency of hysteresis caused heating. Because of this consideration, the exact shape of the hysteresis loop of the material used is not important in the sense that it is relatively unimportant as to whether or not a square wave type of hysteresis type loop is achieved.

It is considered preferable to utilize with the present invention only ferromagnetic particles such as various conventional ferrites and various commercially obtainable iron and steel particles known to have or exhibit comparatively large magnetic losses. It is considered quite fortunate that such materials are relatively inert as far as most metabolic processes are concerned and can be utilized within most parts of the body without significant concern. Other biologically inert particles capable of exhibiting hysteresis heating can, of course, be employed.

An interesting aspect of the invention lies in the fact that magnetic particles may be chosen having a Curie temperature or Curie point such as to control the maximum temperature which can be achieved during induction heating. Thus, for example, it is possible to choose a particular paramagnetic or ferromagnetic composition having a Curie point anywhere within the range of from about 42° C. to about 90° C. specified in the preceding so that hyperthermia of a neoplasm may be accomplished without fear of heating tissue beyond a desired temperature. In connection with this matter, it is noted that normally the magnetic characteristics of a material will change over a comparatively small range of temperatures and that therefore the Curie point in many respects corresponds to a limited range of temperatures.

The particles utilized should be sufficiently small so as to be capable of either going into colloidal suspension within a carrier fluid as subsequently indicated or so as to be capable of forming a slurry with the carrier fluid. Any such a slurry should have a sufficiently low viscosity so as to be capable of being compared with a suspension of aluminum hydroxide antacid in water capable of being easily handled and being poured from a bottle to a spoon and the like. As a practical matter, it is considered that this method of utilization indicates that the particles used should have an average diameter of no greater than about 1 millimeter. It will be realized, however, that on occasion particles which are of slightly larger dimension can be effectively poured and handled.

It is considered that the particles used should not be sufficiently fine so that their fineness will tend to detract from the ability of a magnetic field to cause these particles to heat. In general, if the particles are undesirably small this will tend to make the hysteresis loop exhibited by the material smaller than the loop which would be obtained with somewhat larger sized particles. Because of this, the particles should be of such dimension that there is no diminution of the hysteresis loop exhibited as a result of the size of the particles used. With at least some materials, comparatively long, thin particles appear to have better hysteresis heating characteristics than particles of a reasonably spherical shape.

As a practical matter, it is considered that the lower level of desirable size of the particles used and that the shape of the particles used should be determined on an empirical basis as a result of testing particles of various sizes. Also as a practical matter, it is considered that, in general, the particles used should be of no less dimension than the dimension of the magnetic domains of the material within these particles. In general, it is considered undesirable to utilize particles any finer or smaller than those which are conventionally utilized within ferrofluids in which ferromagnetic particles are held in colloidal suspension.

Within the broad aspects of the present invention, virtually any type of a biologically inert liquid capable of being easily tolerated by the body can be utilized as a carrier fluid so as to facilitate the insertion of magnetic particles as indicated in the preceding. Such a carrier fluid may be of either two broad generalized types. It may be of a type which will remain fluid after being located in place within the body and/or tissue. Such a fluid may be of a type which will form a solid or at least a semi or non-newtonian solid within such tissue.

A carrier fluid of the first type is preferably utilized when particles are to be injected in a location within a neoplasm or even within normal tissue adjacent to neoplasm where there is no reasonable possibility of the particles entering the bloodstream, since there is always a possibility that any such particles in the bloodstream would cause damage. As opposed to this, carriers of the second type which become a solid or semi-solid may be utilized in any location relative to neoplasm—including in blood vessels since the second type of carrier fluid will preclude the movement of particles within the bloodstream by becoming solidified.

Within the broad concepts of the present invention, it is even possible to utilize water as a carrier vehicle in those cases where the particles used will, in effect, be isolated from the remainder of the body by normal tissue surrounding the specific location where such particles are used. Other permanently liquid or at least semi-liquid fluids capable of being utilized are such liquids as Ringer's solution, albumen, essentially fluid-like starch gels and the like. It is not considered necessary to enumerate in this specification many other different carrier fluids which are capable of being utilized within the broad concepts of the present invention inasmuch as various fluids which are compatible with body functioning are well known. When water or any other liquid or semi-liquid carrier is used it is considered that it will be obvious that minor amounts of biologically inert surfactants and the like may be employed so as to facilitate the suspension of the particles used and so as to aid in controlling viscosity of the mixture.

Whenever a carrier is used which will not become solid or semi-solid in time in connection with magnetic particles as noted, it is considered preferable to completely surround such particles with a biologically inert, adherent, conventional protective coating. While in a sense the use of such coated particles is optional, it is nevertheless considered highly preferable to minimize any chance of any sort of unintended interference with normal metabollic processes. Many different types of such coatings are, of course, known. It is considered that coatings such as various polyolefin coatings are particularly suitable. The coatings used on the particles should, of course, be as thin as reasonably possible. A nominal amount of agglomeration of the particles caused by the inherent character of the coating material employed will not normally prove detrimental.

With the present invention it is preferred to utilize a carrier fluid which is of such a character that it will change from a liquid or fluid to essentially a solid or semi-solid after is has been injected into a neoplasm or into a body adjacent to a neoplasm either as a result of a polymerization or similar action initiated as a result of one or more components present in the carrier fluid or as a result of the application of external "energy". Such "energy" may be derived from normal body heat. The energy used may be derived directly from the magnetic field used in causing hysteresis heating or may be the heat resulting from such heating of the particles within the carrier fluid.

The primary reason why the use of a carrier fluid which changes so as to become non-fluid or substantially non-fluid in character is preferred with the present invention relates to the desirability of creating a physical structure within the body which will physically hold the particles used so that such particles cannot move throughout the body in the blood and so that such particles cannot become lodged in various passages or cells where they might cause at least a degree of damage. The precise method or mode of forming a solid or a non-newtonian semi-solid from the mixture of the particles and carrier fluid employed is in many respects immaterial to the present invention.

Further, the solidity of the non-fluid body or composition created is also a matter of choice. From the point of view of patient comfort it is considered that the ultimate non-fluid body created from the carrier fluid should either be of a somewhat flexible, somewhat elastomeric character corresponding to a reasonable degree to the character of human tissue or should be of a non-newtonian character capable of being deformed while still remaining as a coherent body or unit.

As a result of these considerations, it is considered preferable to utilize as the carrier fluid an elastomer which will develop elastomeric, non-fluid properties within the body after being mixed with an amount of particles which is effective so that the complete mixture will in turn be effective in the production of heat by hysteresis heating. Any such fluid composition may contain a wide variety of different biologically inert secondary ingredients such as fumed silica, various surfactants, and the like serving various secondary functions such as, for example, a degree of control of the ultimate elasticity of the polymer body produced. The liquid or fluid composition employed may be a prepolymer or partially polymerized solution containing one or more catalysts. Such a liquid carrier composition may include inert liquid such as water which will not enter into an ultimate or final solid or non-newtonian semi-solid composition but which will serve as a diluent viscosity control agent until such time that the composition becomes non-fluid in character.

It is presently preferred with the present invention to utilize as the carrier fluid a silicone elastomer composition which is capable of being injected into the body as a liquid and which will set up when in place within the body as a polymer serving to physically hold the various magnetic particles used in virtually any intended location within the body. The use of this material is considered to be especially desirable because of the fact that mixtures of this type of composition and of particles as noted are normally adequately coherent so that they will not separate or break up into smaller "units". Further, silicone elastomers as noted herein are normally acceptable for use within the human body.

It is considered quite important that a carrier which is intended to become solid or semi-solid within the body is reasonably able to "wet" various magnetic particles as noted so that such particles are completely coated by the carrier fluid in such a manner that they are effectively isolated from normal body fluids in the final non-fluid body created. This minimizes any chance of the material within the particles used interfering with normal metabolic processes. It also makes it possible to utilize with the invention particles of magnetic material which are somewhat biologically active. The use of any such biologically active material is not, however, preferred because of the possibility of some sort of unintended interference with normal metabolic processes.

The relative proportions of particles and the carrier fluid which should be utilized together in a mixture as described will depend upon the physical properties of the ingredients used. In general, the mixture should contain the minimum amount of the fluid carrier which is effective to suspend and hold the particles so that they will not separate out of the mixture during the time period when the mixture is being injected into a body as indicated in the preceding discussion. Further, the proportions should be such that adequate carrier fluid is present so that the inherent physical cohesive "character" of the fluid will tend to hold the mixture together as a unit after the mixture is injected into the body.

This is considered to be particularly important as, for example, when a mixture as used is inserted into a blood vessel. The mixture should not fragmentize within such a blood vessel but should be of such a character as to hold together as a result of cohesion until such time as it is rendered non-fluid or solidified as indicated in the preceding discussion. In certain applications of the present invention it is highly desirable for the mixture of particles and the fluid carrier to be sufficiently coherent so that such a mixture may to a degree be guided to a specific location or held in such a specific location within or adjacent to neoplasm through the use of an external magnetic fluid until such time as the mixture is rendered sufficiently non-fluid that it is held in place as a result of physical engagement with adjacent walls or tissue.

In some cases, to increase the amount of hysteresis heating attainable at a given magnetic field intensity, it may be desirable to apply a DC magnetic field to the magnetic mixture while it is solidifying. This will align all of the magnetic particles in one direction. Subsequent applications of the AC magnetic field along the same axis will cause more magnetic heating than if the particles were randomly oriented.

In addition, the mixture may contain temperature-indicating ingredients that can be monitored by X-ray, ultrasonic, or other means while the induction heating is in progress.

After a mixture as indicated in the preceding has been located with respect to a neoplasm and, except in those cases where the carrier fluid is "set up" as a result of hysteresis heating as subsequently discussed, the tissue containing the neoplastic growth is subject to an alternating magnetic field as discussed in the preceding which will cause adequate hypertheremia to cause necrosis of the neoplasm adjacent to the magnetic particles present.

Although such heating may be caused with any sort of a coil capable of being utilized for induction heating purposes, it is considered preferable within the concepts of the present invention to utilize a specialized induction heating apparatus 10 as illustrated in the accompanying drawing. For convenience this apparatus 10 is referred to as including circuit components as hereinafter described.

This particular apparatus 10 includes a series of coaxial, identically constructed and dimensioned flat, "pancake" coils 12. Each of these coils 12 consists of a series of turns (not separately numbered) of an electrically non-conductive tube 14 such as an extruded polyvinyl polymer tube located in two flat, parallel planes and a conductor 16 going through the interior of each tube 14. These conductors 16 are sufficiently small so as to permit a cooling liquid such as, for example, a dielectric oil or distilled water to be circulated through the tubes 14 around the conductors 16.

Appropriate conventional fittings 18 are provided at the ends (not separately numbered) of the tubes 14 for the purpose of joining the ends (not separately numbered) of the tubes 14 to manifolds or distributing pipes 20 used in connection with a storage reservoir 22 and a pump 24. These fittings 18 are formed in a conventional or known manner so that the conductors 16 extend through them so that these conductors 16 may be connected as hereinafter indicated.

With the present invention each conductor 16 constitutes the electrically "active" part of a coil 12 and is connected into a tank circuit 26 across two separate capacitors 28 of equal capacitance value located in series with one another. All of the coils 12 and the associated capacitors 28 together constitute a tank circuit having a specific resonant frequency.

A known adjustable power supply 30 capable of being adjusted so as to operate at various frequencies is used as a means for supplying a current at the noted resonant frequency to a transformer 32 which in turn is connected to only one of the tank circuits 26. In the particular embodiment illustrated the transformer 32 is connected across only one of the two capacitors 28 in such a circuit 26. However, if desired, this transformer 32 can be connected across both the capacitors 28 in this particular circuit 26.

All of the circuits 26 are grounded by conventional grounds 34. In order to promote safety it is preferred to ground each circuit 26 between the capacitors 28 in such circuit as shown. With the present invention the particular coil 12 which is driven by the power supply 30 and the transformer 32 may be any one of the individual coils 12 used in the complete apparatus 10.

The coils 12 are assembled closely together as shown in a "stack" of aligned, identical pancake-type coils 12. They preferably are secured together as a unit (not numbered) by the use of a conventional, appropriate adhesive (not shown). Because they are used in this manner, in effect, the coils 12 constitute a series of closely coupled transformer coils. As a consequence of this, the use of the power supply 30 with a single coil 12 has the effect of "driving" the remainder of the coils 12 and, of course, the associated tank circuits 26 including these coils 12.

In order to achieve the degree of hysteresis heating desired with the present invention in connection with a comparatively small area or region of a mixture of a carrier and particles as indicated in the preceding discussion it is necessary to drive the particular circuit 26 connected to the power supply 30 utilizing a comparatively significant amount of power. The exact amount of such power will, of course, vary in accordance with many factors. At this time, it is believed that the exact amount of power used in various different reasonably related treatments of neoplastic tissue should be judged on an emperical basis as an outgrowth of experience, taking into consideration factors as are subsequently indicated.

The frequency of the AC current supplied to a coil 12 and its associated circuit 26 is normally determined on the basis of the factors indicated in the preceding discussion relative to the background of the invention so as to minimize eddy-current type heating losses while concurrently maximizing the efficiency of the hysteresis heating obtained. At this time, it is believed that a frequency of from about 1000 to about 5000 Hz—and preferably of about 2000 Hz—initially represents the most desirable "balance" between competitive factors which are involved in achieving the desired hyperthermia in accordance with the invention and that the individual tank circuits 26 should be formed to a specific frequency as noted and that the power supply 30 should be operated at such frequency.

As power is supplied to a circuit 26 and its associated coil 12 a cooling liquid will, of course, be supplied to the individual coils 12 in an effort to prevent any damaging temperature rise in these coils or their manner of operation. However, in spite of this some heating will normally occur in the individual conductors 16 in the various coils 12 and in connection with the various associated capacitors 28. Because of such heating, the individual circuits 26 will change slightly as they are used and this in turn will affect the resonant frequency of the complete apparatus.

Because of this, as the complete apparatus 10 is operated the frequency of the power supply 30 used to drive directly one circuit 26 and its associated coil 12 and the remainder of the circuits 26 and coils 12 indirectly should be adjusted so as to always match the new resonant frequency of the complete collection of circuits 26. In order to further minimize power losses it is considered highly preferable to utilize as the conductors 16 either wires composed of a twisted multitude of strands of individual wires or conventional Litz wires.

The utilization of such conductors may also be advantageous for another reason. During the use of the coil 12 at high power levels, as indicated, a cooling fluid must be circulated through the tube 16, as previously indicated, so as to prevent damage to either the tubes 14 or melting of the conductor 16. It is considered that the surface configuration of either a twisted or a Litz wire conductor, as noted, is effective in promoting efficient heat transfer from the conductor to the cooling liquid employed.

During the utilization of the apparatus 10 power will be supplied from the power supply 30 to a connected tank circuit 26 at a frequency matching the resonant frequency of all of the circuits 26 as a "unit". As this specific circuit 26 is driven or powered in this manner it will set up a flux field which will in turn couple to the adjacent coils 12 so as to power these adjacent coils in a transformer-like manner by mutual induction. This will have the effect of utilizing one specific coil 12 to drive all of the various coils 12 solely as the result of the mutual induction between the coils 12. This has several significant advantages. First, only comparatively low voltages are required at the terminals of the individual coils since they are electrically in parallel; a series-wound coil of the same total number of turns would require many kilovolts of excitation voltage, with accompanying high-voltage insulation requirements, corona discharge problems, and safety hazards. Second, the circuits 26 are electrically isolated so that they need not all have exactly the same voltage, a requirement that would exist if all of the circuits 26 were connected to a common voltage source.

It is not to be assumed from the above that the apparatus 10 requires the utilization of coils 12 which are symmetrical relative to an axis. In increasing the efficiency of the apparatus 10, it is considered desirable to construct all the coils 12 used so that they are of an identical oval shape such that their interiors reasonably conform to the non-rectilinear shape in a human body. When the interiors of the coils 12 are of such dimension an entire significantly sized segment of the body can be located within them. This is quite important in the treatment of many internal neoplasms located generally within the "trunk" of the body. It is considered significant that apparently the insertion of even the heart within an alternating magnetic field having a frequency as noted does not affect the body to any significant or material extent. As a result of this, an apparatus 10 can be utilized in treating even a neoplasm which is immediately adjacent to or is associated with the heart in one manner or another.

The amount of time that a part of the body is generally within the coils 12 in practicing the present invention will, of course, vary depending upon the total amount of heat or the maximum temperature required in order to cause necrosis of neoplastic growth. When the magnetic particles employed have a Curie point from about 42° C. to about 90° C., excessive overheating will normally be prevented by the loss of magnetic properties of the particles used as they reach a temperature corresponding to their Curie points. When, however, magnetic particles are used which have Curie points above the specific temperature range noted, it is considered highly desirable to carefully monitor the time that a specific area containing magnetic particles is generally within the coils 12 and the power supplied to these coils. Generally speaking, at a specific power level the coils 12 should not be operated any longer than is necessary to cause necrosis of neoplastic tissue. Since this is dependent upon both temperature and time, it is considered desirable to carefully monitor the temperature.

As the apparatus 10 is used, it is obvious that normal cells or tissue adjacent to any magnetic materials or particles present will become heated to at least a degree and that frequently such normal tissue or growth will be necrosed. Normally, this does not present any significant problems. As is well known, the body has what may be regarded as inherent mechanisms for dealing with many different eventualities and is reasonably capable of disposing of both necrosed normal and neoplastic tissue or cells through normal metabollic processes. Further, the body is reasonably capable of developing what may be loosely referred to as scar tissue in compensating for normal growth which has been lost as a result of hyperthermia. Not infrequently, the body, through its own internal mechanisms, will develop barriers of a known or conventional type isolating areas where magnetic particles have been used from the normal metabollic operation of the body.

I claim:

1. An induction heating apparatus having an induction heating coil and a power supply means connected to said heating coil for supplying electric power to said coil in which the improvement comprises:
    a plurality of different coils which are identical to said heating coil,
    each of said coils being a flat "pancake" coil including a series of turns of an electrically non-conductive tube with a multi-strand conductor extending through its interior, this conductor being sufficiently small so as to permit a cooling fluid to be circulated through the interior of the tube within which it is located,
    said coils being located closely adjacent to one another in a "stack" in which said coils are aligned with one another so as to be capable of serving as a series of closely coupled transformer coils,
    manifold means connected to the ends of said tubes of said coils for conveying a cooling fluid through said tubes of said coils,
    a capacitor means connected across the ends of the conductor in each of said coils and said heating coil so as to constitute, in combination with the coil to which it is attached, a tank circuit having a resonant frequency,
    said capacitor means all having equal capacitance values,
    said tank circuits all having the same resonant frequency,
    said power supply means being connected only to said heating coil and the tank circuit associated with said heating coil and capable of supplying power at a frequency which is the same as the resonant frequency of the tank circuits,
    said power supply means being adjustable so that the frequency of the power supplied to the tank circuit to which it is connected can be adjusted in accordance with any change in the resonant frequency of said tank circuits.

2. An induction heating apparatus as claimed in claim 1 wherein:
    said frequency is a frequency of from about 1000 to 5000 Hz.

3. An apparatus as claimed in claim 2 wherein:
    all of said coils are of an identical oval shape such that their interiors reasonably correspond to the non-rectangular shape of the "trunk" of a human body.

4. An induction heating apparatus as claimed in claim 1 including:
   a body having neoplasm therein and immobilized magnetic particles located in proximity to said neo-plasm, said neoplasm and said magnetic particles being located within the interiors of said coils.

5. An induction heating apparatus as claimed in claim 4 wherein: said power supply means is capable of heating said magnetic particles to a temperature sufficient to cause necrosis of said neoplasm.

6. An induction heating apparatus as claimed in claim 5 wherein:
   said frequency is a frequency of from about 1000 to 5000 Hz.

7. An apparatus as claimed in claim 6 wherein:
   all of said coils are of an identical oval shape such that their interiors resonably correspond to the non-rectangular shape of the "trunk" of a human body.

* * * * *